(12) United States Patent
Hunt et al.

(10) Patent No.: US 9,040,920 B1
(45) Date of Patent: May 26, 2015

(54) OPTICAL OBJECT DETECTION SYSTEM

(71) Applicant: The Boeing Company, Chicago, IL (US)

(72) Inventors: Jeffrey H. Hunt, Thousand Oaks, CA (US); Nicholas Koumvakalis, Thousand Oaks, CA (US)

(73) Assignee: The Boeing Company, Chicago, IL (US)

(*) Notice: Subject to any disclaimer, the term of this patent is extended or adjusted under 35 U.S.C. 154(b) by 327 days.

(21) Appl. No.: 13/732,666

(22) Filed: Jan. 2, 2013

(51) Int. Cl.
*G01N 21/01* (2006.01)
*G01J 1/04* (2006.01)

(52) U.S. Cl.
CPC .............. *G01J 1/0407* (2013.01); *G01N 21/01* (2013.01); *G01N 2021/0162* (2013.01)

(58) Field of Classification Search
CPC .. G01V 8/00; G01N 2021/1706; G01N 21/17
See application file for complete search history.

(56) References Cited

U.S. PATENT DOCUMENTS

| | | | |
|---|---|---|---|
| 3,745,575 A | 7/1973 | Kikuchi | |
| 3,775,765 A | 11/1973 | Di Piazza et al. | |
| 3,831,173 A | 8/1974 | Lerner | |
| 5,327,139 A | 7/1994 | Johnson | |
| 5,457,394 A | 10/1995 | McEwan | |
| 5,512,834 A | 4/1996 | McEwan | |
| 5,668,342 A | 9/1997 | Discher | |
| 5,819,859 A | 10/1998 | Stump et al. | |
| 5,900,833 A | 5/1999 | Sunlin et al. | |
| 6,057,765 A | 5/2000 | Jones et al. | |
| 6,060,815 A | 5/2000 | Nysen | |
| 6,094,157 A | 7/2000 | Cowdrick | |
| 6,163,259 A | 12/2000 | Barsumian et al. | |
| 6,501,414 B2 | 12/2002 | Arndt et al. | |
| 6,522,285 B2 | 2/2003 | Stolarczyk et al. | |
| 6,545,945 B2 | 4/2003 | Caulfield | |
| 6,765,527 B2 | 7/2004 | Jablonski et al. | |

(Continued)

FOREIGN PATENT DOCUMENTS

| | | |
|---|---|---|
| WO | WO0077614 A2 | 12/2000 |
| WO | WO2006110991 A1 | 10/2006 |
| WO | WO2009099710 A1 | 8/2009 |

OTHER PUBLICATIONS

Guyot-Sionnest et al., "Surface Polar Ordering in a Liquid Crystal Observed by Optical Second-Harmonic Generation," Physical Review Letters, vol. 57, No. 23, Dec. 8, 1986, pp. 2963-2966.

(Continued)

*Primary Examiner* — Tony Ko
(74) *Attorney, Agent, or Firm* — Yee & Associates, P.C.

(57) ABSTRACT

A method and apparatus for detecting an object. A first optical signal having a first frequency is transmitted to a location on a surface of a ground. A second optical signal having a second frequency is transmitted to the location on the surface of the ground such that the first optical signal and the second optical signal overlap each other at the location on the surface of the ground. The overlap of the first optical signal and the second optical signal at the location generates a third optical signal having a difference frequency that is a difference between the first frequency and the second frequency. The third optical signal is configured to travel into the ground. A response to the third optical signal is detected. A determination is made as to whether an object is present in the ground using the response to the third optical signal.

20 Claims, 5 Drawing Sheets

(56) References Cited

U.S. PATENT DOCUMENTS

| | | |
|---|---|---|
| 6,864,825 B2 | 3/2005 | Holly |
| 6,897,777 B2 | 5/2005 | Holmes et al. |
| 6,943,742 B2 | 9/2005 | Holly |
| 6,950,076 B2 | 9/2005 | Holly |
| 6,999,041 B2 | 2/2006 | Holly |
| 7,009,575 B2 | 3/2006 | Holly et al. |
| 7,142,147 B2 | 11/2006 | Holly |
| 7,190,302 B2 | 3/2007 | Biggs |
| 7,486,250 B2 | 2/2009 | Vetrovec et al. |
| 7,512,511 B1 | 3/2009 | Schultz et al. |
| 7,515,094 B2 | 4/2009 | Keller, III |
| 7,528,762 B2 | 5/2009 | Cerwin |
| 7,595,491 B2 * | 9/2009 | Zhang et al. ............... 250/341.1 |
| 7,777,671 B2 | 8/2010 | Schnitzer et al. |
| 7,893,862 B2 | 2/2011 | Holly et al. |
| 8,035,550 B2 | 10/2011 | Holly et al. |
| 8,054,212 B1 | 11/2011 | Holly et al. |
| 8,275,572 B2 | 9/2012 | Burns et al. |
| 8,289,201 B2 | 10/2012 | Holly et al. |
| 8,299,924 B2 | 10/2012 | Holly et al. |
| 8,653,462 B2 * | 2/2014 | Zhang et al. ............... 250/340 |
| 2005/0062639 A1 | 3/2005 | Biggs |
| 2007/0013577 A1 | 1/2007 | Schnitzer et al. |
| 2007/0024489 A1 | 2/2007 | Cerwin |
| 2009/0040093 A1 | 2/2009 | Holly et al. |
| 2010/0001899 A1 | 1/2010 | Holly et al. |
| 2011/0231150 A1 | 9/2011 | Burns et al. |

OTHER PUBLICATIONS

Heinz et al., "Spectroscopy of Molecular Monolayers by Resonant Second-Harmonic Generation," Physical Review Letters, vol. 48, No. 7, Feb. 15, 1982, pp. 478-481.

Shen, "Surface Second Harmonic Generation: A New Technique for Surface Studies," Ann. Rev. Mater. Sci., vol. 16, Aug. 1986, 19 pages.

Rasing et al., "A Novel Method for Measurements of Second-Order Non-Linearities of Organic Molecules," Chemical Physics Letters, vol. 130, Nos. 1, 2, Sep. 26, 1986, 6 pages.

Hunt et al., "Observation of C—H Stretch Vibrations of Monolayers of Molecules Optical Sum-Frequency Generation," Chemical Physics Letters, vol. 133, No. 3, Jan. 16, 1987, 5 pages.

Berkovic et al., "Study of Monolayer Polymerization Using Nonlinear Optics," J. Chem. Phys., vol. 85, No. 12, Dec. 15, 1986, pp. 7374-7376.

Holly et al., "Multi-Band Receiver Using Harmonic Synchronous Detection," U.S. Appl. No. 12/504,293, filed Jul. 16, 2009, 68 pages.

* cited by examiner

OPTICAL OBJECT DETECTION SYSTEM

BACKGROUND INFORMATION

1. Field

The present disclosure relates generally to detecting objects and, in particular, to detecting objects under the ground. Still more particularly, the present disclosure relates to a method and apparatus for detecting objects under the ground using an optical object detection system.

2. Background

Improvised explosive devices are bombs constructed and deployed in manners not normally used by conventional military organizations. Improvised explosive devices may be used by terrorists, guerillas, and other forces. Improvised explosive devices may be placed under the surface of the ground in a location such as a roadway, a path, or some other location.

An improvised explosive device may have a power supply, a trigger, a detonator, a main charge, and a container. The improvised explosive device also may include shrapnel-generating objects, such as nails or ball bearings.

The trigger is a mechanism used to set off the device. The trigger may be, for example, a radio signal, a tripwire, a timer, or a firing button. Improvised explosive devices have employed cell phones, cordless phones, garage door openers, and/or some other type of electronic device to trigger detonation of the improvised explosive device.

To counter improvised explosive devices, jamming systems have been employed to prevent setting off the improvised explosive devices. Although jamming systems may be used to prevent setting off improvised explosive devices, these types of jamming systems do not detect the presence of an improvised explosive device.

Additionally, various technologies have been used to detect improvised explosive devices. These technologies involve using radar, x-rays, and/or pre-detonators. For example, some detection systems include a stoichiometric diagnostic device. This type of device is capable of deciphering chemical signatures of unknown substances through metal or other barriers. An example of another detection device is a laser-induced breakdown spectroscopy system. This type of system is capable of detecting traces of explosives used for improvised explosive devices from distances, such as around 30 meters. Some improvised explosive devices, however, may not emit chemicals or have detectable amounts of explosives.

Therefore, it would be desirable to have a method and apparatus that takes into account at least some of the issues discussed above, as well as other possible issues.

SUMMARY

In one illustrative embodiment, an apparatus comprises a transmitter system and a receiver system. The transmitter system is configured to transmit a first optical signal having a first frequency and a second optical signal having a second frequency to a location on a surface of a ground such that the first optical signal and the second optical signal overlap each other at the location on the surface of the ground. The overlap of the first optical signal and the second optical signal at the location on the surface of the ground generates a third optical signal having a difference frequency that is a difference between the first frequency and the second frequency. The third optical signal is configured to travel into the ground. The receiver system is configured to detect a response to the third optical signal.

In another illustrative embodiment, a method for detecting an object is presented. A first optical signal having a first frequency is transmitted to a location on a surface of a ground. A second optical signal having a second frequency is transmitted to the location on the surface of a ground such that the first optical signal and the second optical signal overlap each other at the location on the surface of the ground. The overlap of the first optical signal and the second optical signal at the location on the surface of the ground generates a third optical signal having a difference frequency that is a difference between the first frequency and the second frequency. The third optical signal is configured to travel into the ground. A response to the third optical signal is detected. A determination is made as to whether an object is present in the ground using the response to the third optical signal.

The features and functions can be achieved independently in various embodiments of the present disclosure or may be combined in yet other embodiments in which further details can be seen with reference to the following description and drawings.

BRIEF DESCRIPTION OF THE DRAWINGS

The novel features believed characteristic of the illustrative embodiments are set forth in the appended claims. The illustrative embodiments, however, as well as a preferred mode of use, further objectives and features thereof, will best be understood by reference to the following detailed description of an illustrative embodiment of the present disclosure when read in conjunction with the accompanying drawings, wherein:

DETAILED DESCRIPTION

The illustrative embodiments recognize and take into account one or more different considerations. For example, the illustrative embodiments recognize and take into account that difference frequency radar systems may be used to transmit two beams into the ground. A nonlinear target under the ground may generate a response when the beams intersect at the nonlinear target under the ground. This response is a difference frequency that may be detected.

The illustrative embodiments also recognize and take into account that this type of detection system relies on the object under the ground having nonlinear electrical properties. In these illustrative examples, these nonlinear electrical properties may include at least one of conductive, capacitive, inductive, and other types of electrical properties.

As used herein, the phrase "at least one of", when used with a list of items, means different combinations of one or more of the listed items may be used and only one of each item in the list may be needed. For example, "at least one of item A, item B, and item C" may include, without limitation, item A or item A and item B. This example also may include item A, item B, and item C or item B and item C.

For example, the nonlinear electrical properties of the object may be any number of properties in which current does not have a linear relationship with voltage. In these illustrative examples, the nonlinear electrical properties may result from two different types of metal layers in the object. For example, a corroded or oxidized portion of the surface of the object that has a different electrical characteristic from a non-corroded or non-oxidized portion of the object may be used.

The illustrative embodiments recognize and take into account that the composition of the ground may also have nonlinear electrical properties that may distort the radio frequency signals. The illustrative embodiments recognize and take into account that the properties in the ground may distort these beams such that a signal with the difference frequency is not generated by the beams when encountering the object. Further, the use of this type of detection system requires the object to have nonlinear electrical properties.

Thus, other types of objects may not be detected using these types of systems. For example, a plastic object with contraband that does not have nonlinear electrical properties may not be detected by this type of system.

Thus, the illustrative embodiments provide a method and apparatus for detecting objects under the ground. In one illustrative example, an apparatus comprises a transmitter system and a receiver system.

The transmitter system is configured to transmit a first optical signal having a first frequency and a second optical signal having a second frequency. The first optical signal and the second optical signal are transmitted to a location on the surface of the ground. This transmission is such that the first optical signal and the second optical signal overlap each other at the location on the surface of the ground.

The overlap of the first optical signal and the second optical signal on the surface of the ground at the location causes a third optical signal to be created. The third optical signal is configured to travel into the ground. The third optical signal has a difference frequency that is the difference between the first frequency and the second frequency.

The receiver system is configured to detect a response to the third optical signal. In these illustrative examples, this response to the third optical signal may be caused by an object under the ground. A determination may then be made as to whether an object is present in the ground and the object may be identified from the response to the third optical signal.

Figure 1:
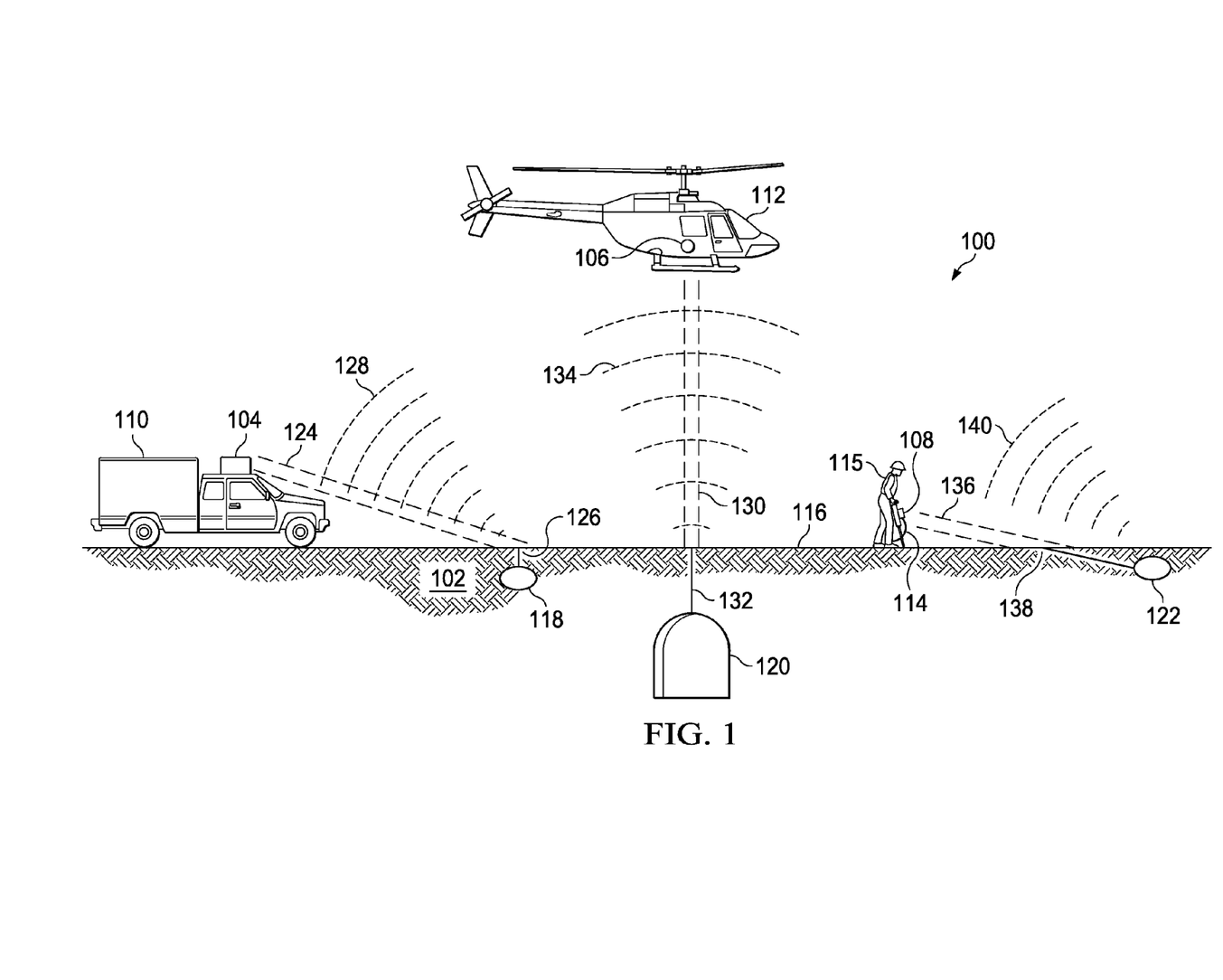
FIG. 1 is an illustration of an object detection environment in accordance with an illustrative embodiment.

With reference now to the figures and, in particular, with reference to FIG. 1, an illustration of an object detection environment is depicted in accordance with an illustrative embodiment. In this depicted example, object detection environment 100 is an environment in which optical object detection systems may be used to detect objects under ground 102.

In this illustrative example, three optical object detection systems are shown in object detection environment 100. These optical object detection systems include optical object detection system 104, optical object detection system 106, and optical object detection system 108. These optical object detection systems are associated with different types of platforms.

When one component is "associated" with another component, the association is a physical association in the depicted examples. For example, a first component may be considered to be associated with a second component by being secured to the second component, bonded to the second component, mounted to the second component, welded to the second component, fastened to the second component, and/or connected to the second component in some other suitable manner. The first component also may be connected to the second component using a third component. The first component may also be considered to be associated with the second component by being formed as part of and/or an extension of the second component.

As depicted, optical object detection system 104 is associated with truck 110. Optical object detection system 106 is associated with rotorcraft 112, and optical object detection system 108 is associated with portable frame 114. In this illustrative example, portable frame 114 may be operated by human operator 115. As depicted, these optical object detection systems may be used to detect objects below surface 116 of ground 102. In some illustrative examples, truck 110, rotorcraft 112, and portable frame 114 may be considered part of the optical object detection systems.

In this illustrative example, object 118 may be, for example, an improvised explosive device under ground 102. Object 120 may be a tunnel under ground 102. Object 122 may be contraband or some illegal device or substance under ground 102.

As depicted, optical object detection system 104 is configured to generate optical signals 124 in the form of two collimated light beams. In these illustrative examples, optical signals 124 interact with ground 102 at surface 116 of ground 102 to form optical signal 126. In particular, the collimated light beams interact with each other in the presence of ground 102. In other words, ground 102 is a medium that mediates or facilitates the interaction of the collimated light beams with each other to form optical signal 126.

Optical signal 126 has a difference frequency based on the difference between the frequencies of the two collimated light beams in optical signals 124. Optical signal 126 is configured to travel through ground 102. In this depicted example, response 128 may occur when optical signal 126 encounters object 118. For example, optical signal 126 may reflect off object 118 to form response 128. Response 128 may be detected by optical object detection system 104.

Optical object detection system 106 is configured to generate optical signals 130 in the form of two collimated light beams. As depicted, optical signals 130 may interact with ground 102 at surface 116 of ground 102. This interaction forms optical signal 132. Optical signal 132 has a difference frequency based on the difference between the frequencies of the two collimated light beams. Optical signal 132 is configured to travel through ground 102. When optical signal 132 encounters object 120, response 134 is generated. Response 134 may be a reflection of optical signal 132 off object 120. Response 134 may be detected by optical object detection system 106.

In a similar fashion, optical object detection system 108 is configured to generate optical signals 136 in the form of two collimated light beams. Optical signals 136 may result in optical signal 138 when the two collimated light beams in optical signals 136 interact with ground 102 at surface 116 of ground 102. Optical signal 138 is configured to travel through ground 102. When optical signal 138 encounters object 122, response 140 is generated. In this example, response 140 is a reflection of optical signal 138 off object 122. Response 140 may be detected by optical object detection system 108.

In this manner, optical object detection system 104, optical object detection system 106, and optical object detection system 108 may be used to detect objects under ground 102. These optical object detection systems may detect objects more easily as compared to currently used detection systems.

Figure 2:
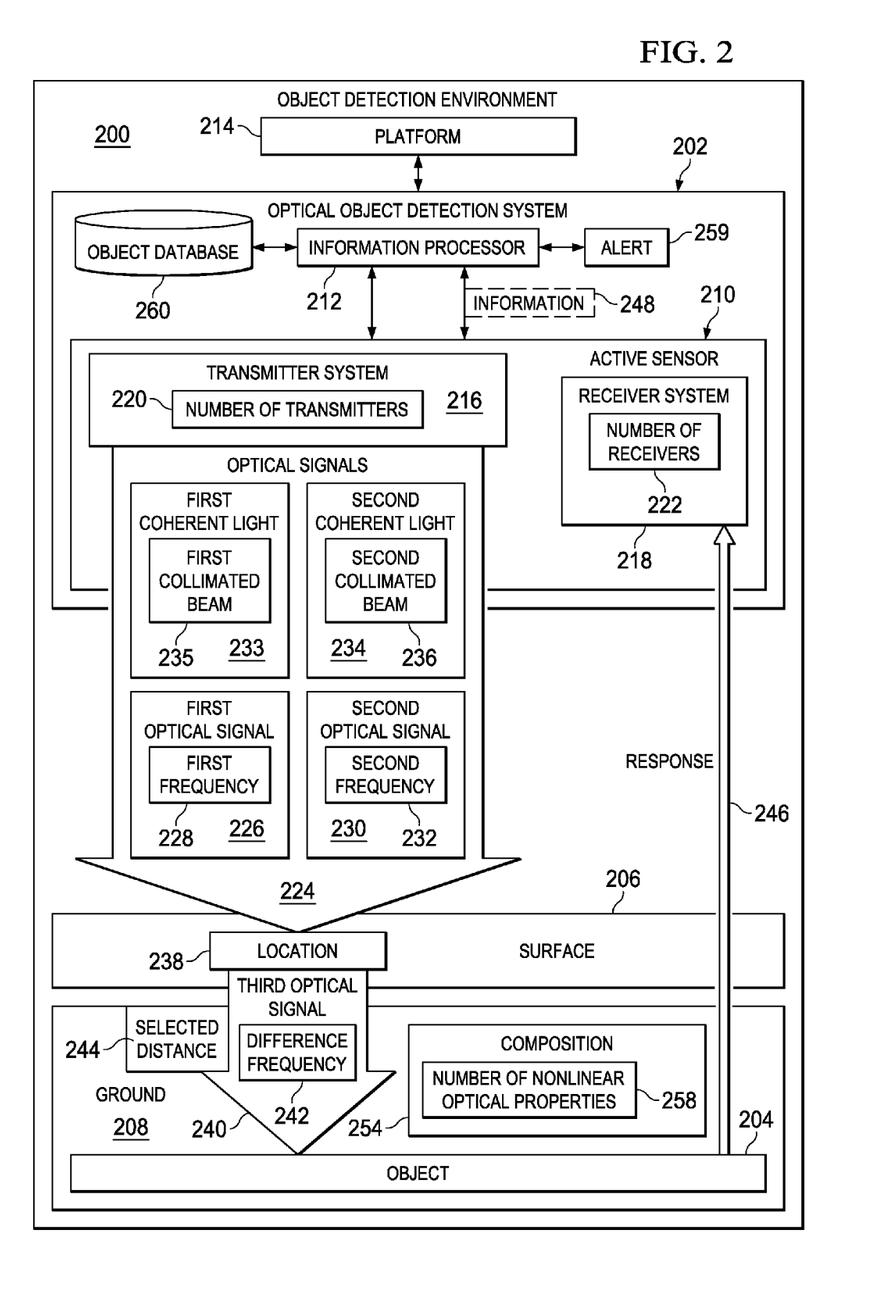
FIG. 2 is an illustration of a block diagram of an object detection environment in accordance with an illustrative embodiment.

Turning now to FIG. 2, an illustration of a block diagram of an object detection environment is depicted in accordance with an illustrative embodiment. Object detection environment 100 in FIG. 1 is an example of one implementation of object detection environment 200 shown in block form in FIG. 2.

In this depicted example, optical object detection system 202 may be used to detect object 204. Object 204 is located under surface 206 of ground 208 in this particular example.

As depicted, object 204 may take various forms. For example, object 204 may be a steel container, a plastic container, an improvised explosive device, contraband, a box, a tunnel, a pipe, a wire, a cable, a container, and other types of objects for which detection may be desired.

In these illustrative examples, detecting object 204 may comprise detecting a presence of object 204. Additionally, detecting object 204 also may include identifying object 204. Identifying object 204 includes determining a type of object for object 204. For example, identifying object 204 may include determining whether object 204 is a pipe, an improvised explosive, device, or some other type of object.

As depicted, optical object detection system 202 may be comprised of a number of different components. For example, optical object detection system 202 comprises active sensor 210 and information processor 212.

Further, optical object detection system 202 may be associated with platform 214. Platform 214 may take various forms. For example, platform 214 may be selected from one of a truck, a rotorcraft, an unmanned aerial vehicle, a portable frame, an unmanned ground vehicle, and other suitable types of platforms.

In this illustrative example, active sensor 210 may be comprised of transmitter system 216 and receiver system 218. Transmitter system 216 may include number of transmitters 220 and receiver system 218 may include number of receivers 222. A number, as used herein with reference to items, is one or more items. For example, number of receivers 222 is one or more receivers.

Transmitter system 216 is configured to generate optical signals 224. In particular, transmitter system 216 is configured to generate first optical signal 226 having first frequency 228 and second optical signal 230 having second frequency 232. In these illustrative examples, an optical signal in optical signals 224 is an electromagnetic signal that may include at least one of visible light, ultraviolet light, and infrared light.

Ultraviolet light may have a wavelength from about 400 nm to about 10 nm. Visible light may have a wavelength from about 760 nm to 380 nm. Infrared light may have a wavelength from about 750 nm to about 1 mm.

In these illustrative examples, transmitter system 216 may be configured to generate first optical signal 226 as first coherent light 233 and second optical signal 230 as second coherent light 234. Further, transmitter system 216 may be configured to generate first optical signal 226 such that first optical signal 226 is in the form of first collimated beam 235. In a similar fashion, transmitter system 216 is configured to generate second optical signal 230 in the form of second collimated beam 236.

In other words, first optical signal 226 may be first collimated beam 235 of first coherent light 233 and second optical signal 230 may be second collimated beam 236 of second coherent light 234. In this illustrative example, first collimated beam 235 and second collimated beam 236 have substantially the same intensities. Of course, in other illustrative examples, first collimated beam 235 and second collimated beam 236 may have different intensities.

The selection of intensities for first collimated beam 235 and second collimated beam 236 may affect third optical signal 240. For example, higher peak intensities may result in more efficient mixing between first collimated beam 235 and second collimated beam 236.

Further, the selection of polarization for first collimated beam 235 and second collimated beam 236 may also affect the mixing between first collimated beam 235 and second collimated beam 236 to form third optical signal 240. In these illustrative examples, beam polarizations are defined as "P" or "S" depending on whether the beams are polarized in the plane or perpendicular to the plane of incidence. Polarization combinations of P-P, P-S, S-P may provide a desired difference frequency generation to form third optical signal 240. In these illustrative examples, a polarization of S-S combination cannot cause difference frequency generation to generate third optical signal 240 at the surface.

A collimated beam is comprised of electromagnetic radiation in the form of rays that are substantially parallel. A collimated beam tends to spread more slowly as the electromagnetic radiation propagates as compared to electromagnetic radiation that has not been collimated.

In these illustrative examples, transmitter system 216 is configured to transmit first optical signal 226 and second optical signal 230 to location 238 on surface 206 of ground 208. The directing of first optical signal 226 and second optical signal 230 is such that first optical signal 226 and second optical signal 230 overlap each other at location 238 on surface 206 of ground 208.

This overlap of first optical signal 226 and second optical signal 230 at surface 206 of ground 208 at location 238 is configured to cause third optical signal 240 to be generated. Third optical signal 240 may be generated from the interaction of first optical signal 226 and second optical signal 230 with ground 208 at location 238. In particular, in this illustrative example, third optical signal 240 is a nonlinear response created at or near surface 206 of ground 208 where first optical signal 226 and second optical signal 230 overlap with each other.

More specifically, third optical signal 240 is a result of nonlinear mixing of first optical signal 226 and second optical signal 230 facilitated by ground 208. In this case, ground 208 has number of nonlinear optical properties 258 in location 238.

In these illustrative examples, many materials present in ground 208 have some level of nonlinearity for number of nonlinear optical properties 258. This nonlinearity may be the case with the type of complex molecules that exist in ground 208. Materials that have internal symmetry in ground 208 do not have nonlinearity in the illustrative examples. For example, a nitrogen molecule, $N_2$, will not have an inherent nonlinearity. With nonlinear molecules in the ground, phase-matching is another consideration described in more detail below. The phase-matching occurs at the interface between the air and the ground. In this illustrative example, the interface is surface 206 of ground 208.

Third optical signal 240 has difference frequency 242. Difference frequency 242 is a difference between first frequency 228 and second frequency 232. In particular, difference frequency 242 may be selected such that third optical signal 240 is able to travel through ground 208 for selected distance 244.

Selected distance 244 may vary depending on the particular implementation. For example, selected distance 244 may be 4 cm, 10 cm, 15 cm, or some other suitable distance into ground 208.

In these illustrative examples, when third optical signal 240 encounters object 204 under surface 206 of ground 208, response 246 may be generated. Response 246 is a reflection of third optical signal 240 in this illustrative example. Response 246 may travel back through ground 208 and above surface 206.

As depicted, receiver system 218 is configured to detect response 246 when response 246 is generated by third optical signal 240 encountering object 204. Receiver system 218 may generate information 248 when response 246 is detected.

In these illustrative examples, information 248 may indicate that an object below surface 206 of ground 208 caused response 246. In other illustrative examples, information 248 also may indicate how far below ground 208 that object 204 is located. For example, the time of transmission and the time at which the response is detected may be used to identify a distance below ground 208 for object 204. In still other illustrative examples, information 248 may include a shape of object 204 derived from response 246.

Information processor 212 is configured to control the operation of transmitter system 216 and receiver system 218 in active sensor 210. In this illustrative example, information processor 212 may be implemented in hardware and may also be implemented in software. When software is used, the operations performed by information processor 212 may be implemented in program code configured to run on a processor unit. When hardware is employed, the hardware may include circuits that operate to perform the operations in information processor 212.

In these illustrative examples, the hardware may take the form of a circuit system, an integrated circuit, an application specific integrated circuit (ASIC), a programmable logic device, or some other suitable type of hardware configured to perform a number of operations. With a programmable logic device, the device is configured to perform the number of operations. The device may be reconfigured at a later time or may be permanently configured to perform the number of operations. Examples of programmable logic devices include, for example, a programmable logic array, a programmable array logic, a field programmable logic array, a field programmable gate array, and other suitable hardware devices. Additionally, the processes may be implemented in organic components integrated with inorganic components and/or may be comprised entirely of organic components excluding a human being. For example, the processes may be implemented as circuits in organic semiconductors.

For example, information processor 212 may be configured to control transmitter system 216 to select first frequency 228 for first optical signal 226 and second frequency 232 for second optical signal 230. The selection of first frequency 228 and second frequency 232 may be made to obtain a desired value for difference frequency 242 of third optical signal 240.

In these illustrative examples, information processor 212 may select difference frequency 242 such that third optical signal 240 travels into ground 208 toward object 204. Difference frequency 242 may be selected based on composition 254 of ground 208. In these illustrative examples, composition 254 may include at least one of soil, sand, gravel, clay, and other materials.

Composition 254 may have number of nonlinear optical properties 258. Number of nonlinear optical properties 258 may result in the generation of difference frequency 242 for third optical signal 240 from first optical signal 226 and second optical signal 230 interacting with ground 208 at location 238.

Difference frequency 242 also may be based on object 204. For example, if a search is performed to detect a particular type of object, difference frequency 242 may be selected such that third optical signal 240 is reflected off object 204 in a manner such that response 246 can be detected by receiver system 218.

In these illustrative examples, different objects will have different levels of reflectivity. For example, a metal object will reflect third optical signal 240 with almost any frequency for difference frequency 242. Non-metallic objects will reflect less amounts of third optical signal 240. Non-metallic objects may have spectroscopic features that can enhance the reflectance of the object. As a result, some frequencies for difference frequency 242 may reflect in a manner that provides a better quality for response 246 as compared to other frequencies for difference frequency 242.

In the illustrative examples, one manner in which difference frequency 242 may be selected may involve holding the first frequency 228 constant and scanning second frequency 232. In this manner, difference frequency 242 may change the difference frequency. The propagation of third optical signal 240 into the ground varies with changes in difference frequency 242. This type of selection of difference frequency 242 may be used as a discriminator for different objects.

For example, improvised explosive devices are closer to surface 206 of ground 208, while mines, wires, or tunnels are deeper in ground 208. When response 246 to third optical signal 240 is generated closer to the surface, response 246 may indicate the presence of an improvised explosive device. When response 246 to third optical signal 240 is deeper, this response may indicate a presence of a tunnel.

Additionally, information processor 212 also may control the operation of transmitter system 216 such that transmitter system 216 transmits first optical signal 226 and second optical signal 230 in a desired direction. For example, information processor 212 may control transmitter system 216 such that transmitter system 216 transmits first optical signal 226 and second optical signal 230 to location 238. In particular, first optical signal 226 may be first collimated beam 235 of first coherent light 233 and second optical signal 230 may be second collimated beam 236 of second coherent light 234. First collimated beam 235 and second collimated beam 236 may be directed toward location 238 such that first collimated beam 235 and second collimated beam 236 overlap on surface 206 of ground 208 at location 238.

Additionally, information processor 212 may receive information 248 from receiver system 218 when receiver system 218 detects response 246 to third optical signal 240. If the analysis of information 248 indicates a presence of object 204, information processor 212 may generate alert 259. Alert 259 may be at least one of a message, a sound, a light, a graphical indicator, and other suitable types of alerts that indicate the presence of object 204.

Further, information processor 212 also may use information 248 to identify object 204. The identification may include identifying at least one of the type of object, the composition of the object, and other suitable types of information. For example, information 248 may be compared to object database 260. Object database 260 may include example responses for known objects. In this manner, a comparison of information 248 may be used to determine whether response 246 matches an object in object database 260. If a match is present, then the object may be identified as a particular type of object. If the match is absent, the object may be identified as an unknown object. In this manner, information processor 212 may detect and classify object 204 under surface 206 of ground 208 from response 246 detected by receiver system 218.

In this manner, optical object detection system 202 in FIG. 2 may be used to detect objects such as object 204 located under surface 206 of ground 208. With the use of frequencies used for electromagnetic energy in the form of light, increased distance may be achieved as compared to other types of electromagnetic energy such as microwaves. The generation of these optical signals does not rely on the properties of the object that may be detected as compared to currently used techniques that involve electromagnetic signals such as microwaves.

Figure 3:
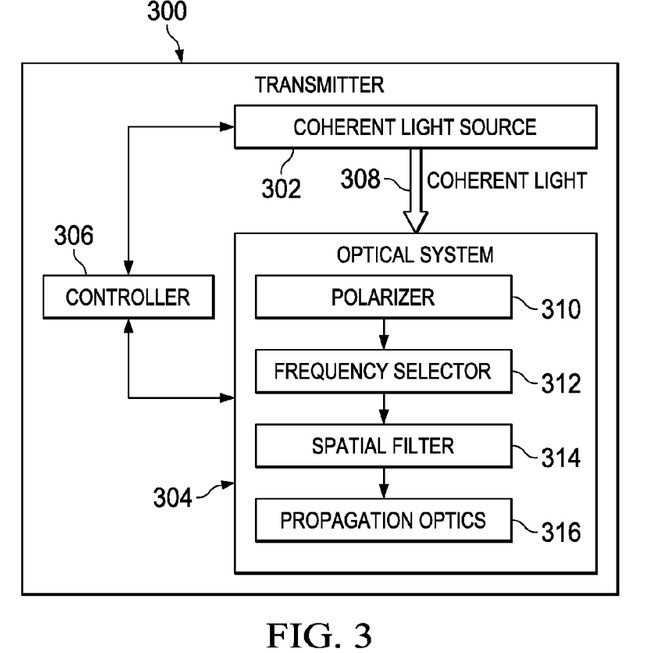
FIG. 3 is an illustration of a block diagram of a transmitter in accordance with an illustrative embodiment.

Turning now to FIG. 3, an illustration of a block diagram of a transmitter is depicted in accordance with an illustrative embodiment. In this illustrative example, transmitter 300 is an example of an implementation for a transmitter in number of transmitters 220 in transmitter system 216 in FIG. 2.

Transmitter 300 may be used to generate optical signals 224 in FIG. 2. In particular, transmitter 300 may be used to generate first optical signal 226 or second optical signal 230 in FIG. 2. In other words, a transmitter such as transmitter 300 may be used to generate each of first optical signal 226 and second optical signal 230 in FIG. 2.

Transmitter 300 is a hardware system that includes a number of different hardware components. For example, transmitter 300 includes coherent light source 302, optical system 304, and controller 306.

Coherent light source 302 is configured to generate coherent light 308 such as light for a laser beam. In this illustrative example, coherent light source 302 sends coherent light 308 to optical system 304.

As depicted, optical system 304 includes a number of different components. As depicted, optical system 304 comprises polarizer 310, frequency selector 312, spatial filter 314, and propagation optics 316.

Polarizer 310 is a hardware device configured to provide a desired polarization for coherent light 308 in these illustrative examples. For example, polarizer 310 may be implemented using one or more light filters in these examples. For example, polarizer 310 may be configured to cause a first polarization in first coherent light 233 and a second polarization in second coherent light 234 in FIG. 2.

Frequency selector 312 is configured to select the desired frequency for coherent light 308. In other words, only portions of coherent light 308 having the desired frequency pass through frequency selector 312. In these illustrative examples, frequency selector 312 may be implemented using one or more wavelength discriminators. The wavelength discriminator used in frequency selector 312 may be, for example, a Bragg grating or some other suitable device.

Spatial filter 314 is configured to improve the quality of coherent light 308. Spatial filter 314 also may be used to reduce or eliminate fringes in the intensity profile for coherent light 308. In these illustrative examples, coherent light 308 takes the form of a laser beam.

Propagation optics 316 are the different components configured to transmit coherent light 308 from transmitter 300. For example, propagation optics 316 may include mirrors, lenses, and other suitable components.

Controller 306 is configured to control the operation of the different components in transmitter 300. For example, controller 306 is configured to control when coherent light source 302 generates and sends coherent light 308 to optical system 304.

Further, controller 306 also may control the operation of different components in optical system 304. In these illustrative examples, controller 306 may be implemented using a hardware device and may include software. For example, controller 306 may be implemented using one or more circuits.

In these illustrative examples, controller 306 may control the operation of polarizer 310 to polarize coherent light 308 to different polarizations. Further, controller 306 also may control the operation of frequency selector 312. For example, if frequency selector 312 includes wavelength discriminators, controllers 306 may control which wavelength discriminator is used to select the wavelength or which frequency is used for passing coherent light 308.

Figure 4:
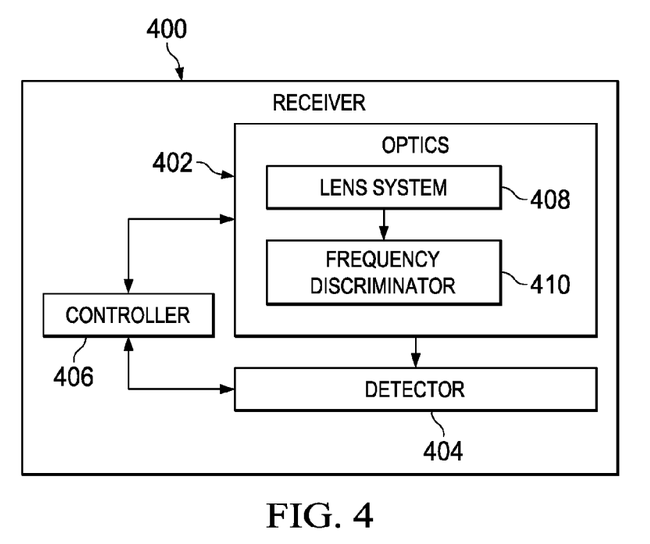
FIG. 4 is an illustration of a block diagram of a receiver in accordance with an illustrative embodiment.

Turning now to FIG. 4, an illustration of a block diagram of a receiver is depicted in accordance with an illustrative embodiment. Receiver 400 is an example of an implementation for a receiver in number of receivers 222 in receiver system 218 in FIG. 2.

As illustrated, receiver 400 is a hardware device and includes a number of different hardware components. As depicted, receiver 400 comprises optics 402, detector 404, and controller 406.

Optics 402 include lens system 408 and frequency discriminator 410. Lens system 408 is configured to detect and receive light from the environment around receiver 400.

Frequency discriminator 410 is configured to pass light that has a number of frequencies. The number of frequencies may be a single frequency, or may be a range of frequency that may be continuous or discontinuous depending on the particular implementation. For example, the number of frequencies may be frequencies that are expected for a difference frequency from a response to optical signals transmitted by a transmitter. Frequency discriminator 410 also may be implemented using a Bragg grating in these illustrative examples.

Detector 404 is a light detection system and is configured to generate electrical signals in response to detecting light that passes through frequency discriminator 410. Detector 404 may be at least one of a photo detector, a charge-coupled device, and some other suitable type of device.

Controller 406 is a hardware device and is configured to control operation of the different components in receiver 400. For example, controller 406 may control the operation of frequency discriminator 410. If more than one Bragg grating is present, controller 406 may control which Bragg grating receives light from optics 402. For example, controller 406 may control the configuration of optics 402, the position of Bragg gratings, or both the configuration of optics 402 and the position of Bragg gratings to determine what frequency of light is passed to detector 404.

Further, controller 406 also may generate information from the electrical signals from detector 404. This information may be information 248 and may be transmitted to information processor 212 in FIG. 2.

The illustration of object detection environment 200 and the different components in FIGS. 2-4 are not meant to imply physical or architectural limitations to the manner in which an illustrative embodiment may be implemented. Other components in addition to or in place of the ones illustrated may be used. Some components may be unnecessary. Also, the blocks are presented to illustrate some functional components. One or more of these blocks may be combined, divided, or combined and divided into different blocks when implemented in an illustrative embodiment.

For example, although transmitter 300 is described as only generating one optical signal in optical signals 224, other implementations of an illustrative embodiment may configure transmitter 300 to generate both first optical signal 226 and second optical signal 230.

Figure 5:
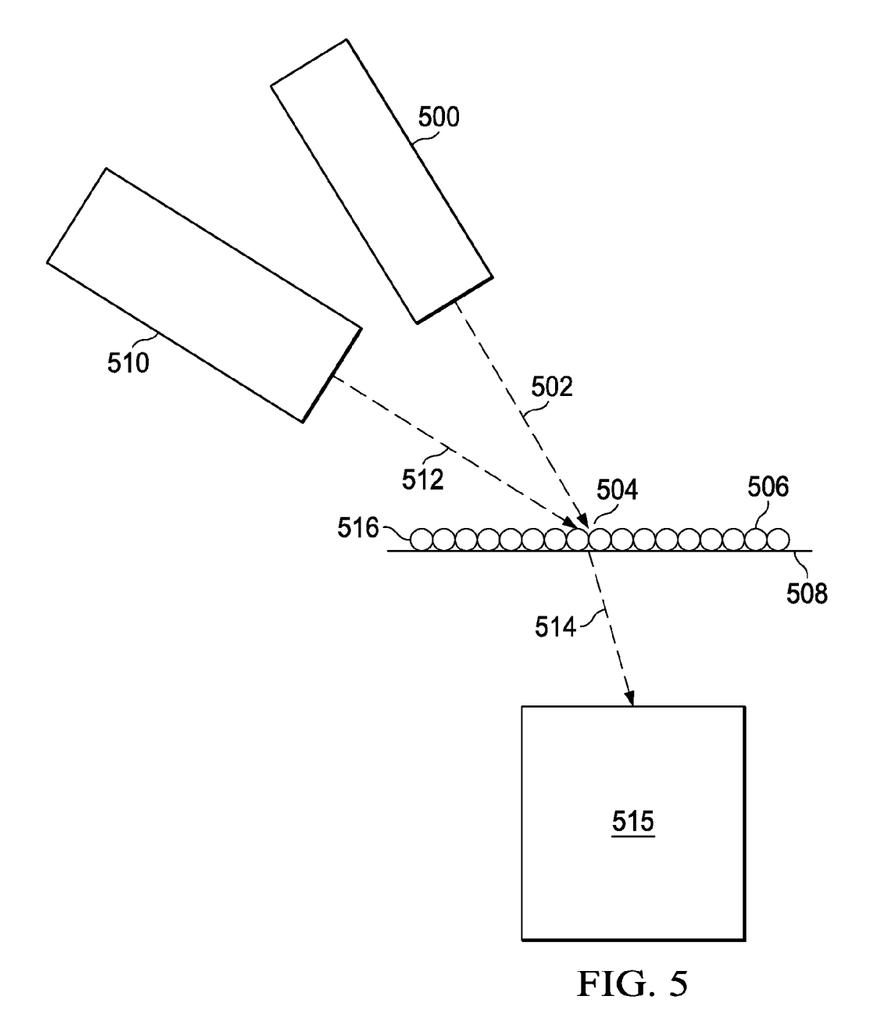
FIG. 5 is an illustration of the generation of a third optical signal from a first optical signal and a second optical signal in accordance with an illustrative embodiment.

With reference now to FIG. 5, an illustration of the generation of a third optical signal from a first optical signal and a second optical signal is depicted in accordance with an illustrative embodiment. In this illustrative example, first source 500 transmits first optical signal 502 toward location 504 on surface 506 of ground 508. Second source 510 transmits second optical signal 512 toward location 504 on surface 506 of ground 508. First source 500 and second source 510 may be located in one or more transmitters in these illustrative examples.

As illustrated, first optical signal 502 and second optical signal 512 may take the form of collimated beams of coherent light such as laser beams. First optical signal 502 and second optical signal 512 overlap each other at location 504 on surface 506 of ground 508.

In these illustrative examples, difference frequency generation occurs where first optical signal 502 and second optical signal 512 overlap each other at surface 506 of ground 508 in location 504. Ground 508 is the medium in which frequency difference generation may occur.

As depicted, ground 508 has one or more nonlinear properties. These nonlinear properties may result in difference frequency generation in third optical signal 514. In this illustrative example, third optical signal 514 may travel through ground 508 to reach object 515.

In these examples, the difference frequency generation results from the nonlinear polarization $\vec{P}^{(2)}(\omega_3=\omega_1-\omega_2)$ in the medium. In this case, the medium is ground 508 at or near surface 506. Nonlinear polarization may be expressed as follows:

$$\vec{P}^{(2)}(\omega_3=\omega_1-\omega_2)=\vec{\chi}^{(2)}(\omega_3=\omega_1-\omega_2): \vec{E}(\omega_1)\vec{E}(\omega_2), \quad (1)$$

where $\vec{P}^{(2)}(\omega_3=\omega_1-\omega_2)$ is the nonlinear polarization, $\omega_1$ is the frequency of first optical signal 502, $\omega_2$ is the frequency of second optical signal 512, $\omega_3$ is the difference frequency, $\vec{\chi}^{(2)}(\omega_3=\omega_1-\omega_2)$ are coefficients with a second order of susceptibility for ground 508, $\vec{E}(\omega_1)$ is the electric field for first optical signal 502, and $\vec{E}(\omega_2)$ is the electrical field for second optical signal 512. If the medium has an inversion symmetry, then the nonlinear susceptibility $\vec{\chi}^{(2)}$ vanishes in the electric-dipole approximation. The existence of a symmetry center may be found where any (x,y,z) point is indistinguishable from a (-x,-y,-z) point. A point on a surface does not have inversion symmetry, because looking up from the ground is very different from looking down at the ground.

Since the inversion symmetry is necessarily broken at an interface, this makes difference frequency generation possible at the surface of the ground. For the purposes of estimating the signal strength, monolayer of molecules 516 is shown at surface 506. The surface nonlinear susceptibility is typically $10^{-15}$ esu, which should yield a difference frequency generation signal of $10^3$ photons/pulse with a laser pulse of 10 mJ energy and 10 nsec duration impinging on a surface area of 0.2 cm$^2$.

The resonant behavior of $\vec{\chi}^{(2)}$ can use surface spectroscopic properties to enhance generation. In the difference frequency generation process, one source beam may be tuned to a surface resonance. The nonlinear susceptibility responsible for the difference frequency generation can be written as:

$$\vec{\chi}^{(2)}(\omega_3=\omega_2-\omega_1)=N_s<\alpha^{(2)}(\omega_1)>, \quad (2)$$

where $N_s$ is the surface density of molecular adsorbates, $\alpha^{(2)}$ is the nonlinear polarizability, and < > denotes an average over the molecular orientation distribution. In general, $\alpha^{(2)}$ consists of a resonant and a non-resonant part that can be expressed as:

$$\alpha^{(2)}=\alpha_R^{(2)}+\alpha_{NR}^{(2)}, \quad (3)$$

with the implication that there will always be some level of nonlinearity in the molecules on the ground surface.

When a phase matching condition is satisfied, difference-frequency generation may occur more efficiently. The phases for the optical signals are expressed as follows:

$$h\vec{k}_3=h\vec{k}_1-h\vec{k}_2 \quad (4)$$

where h is Planck's constant, $\vec{k}_1$ is a wavevector for first optical signal 502, $\vec{k}_2$ is a wavevector for second optical signal 512, and $\vec{k}_3$ is a wavevector for third optical signal 514. These wavevectors are for the three waves in the three optical signals as they travel through the medium. Equation 4 is the optical equivalent of conservation of energy. The wavevectors in the equation are vector quantities and are calculated as such.

For surface 506, each wave vector is the projection of the wavevector onto surface 506, analogous to Snell's law. Since efficient generation only occurs in the direction that this condition is satisfied, the difference frequency generation signal will be very strongly collimated, with propagation characteristics that are the same, as the input becomes more and more efficient. The result is a propagation geometry as illustrated schematically this figure.

Figure 6:
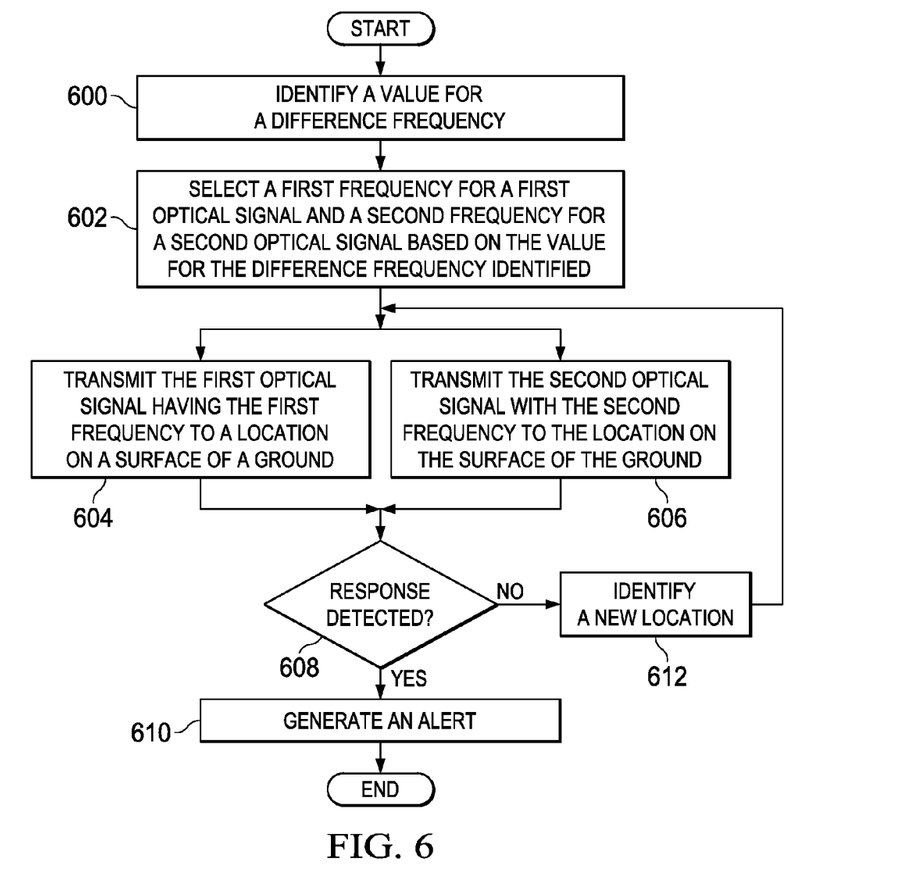
FIG. 6 is an illustration of a flowchart of a process for detecting an object in accordance with an illustrative embodiment.

Turning now to FIG. 6, an illustration of a flowchart of a process for detecting an object is depicted in accordance with an illustrative embodiment. The process illustrated in FIG. 6 may be implemented in object detection environment 200 using optical object detection system 202 in FIG. 2.

The process begins by identifying a value for a difference frequency (operation 600). The value may be identified based on at least one of a number of properties of the ground and a number of properties of the object. In these illustrative examples, the number of properties of the ground may be a number of nonlinear optical properties.

The process then selects a first frequency for a first optical signal and a second frequency for a second optical signal based on the value for the difference frequency identified (operation 602). The process then transmits the first optical signal having the first frequency to a location on a surface of a ground (operation 604). The process also transmits the second optical signal with the second frequency to the location on the surface of the ground (operation 606). As depicted, operation 604 and operation 606 occur at substantially the same time in these illustrative examples. The interaction of the first optical signal and the second optical signal at the location on the surface of the ground results in a third optical signal being generated that has a difference frequency in which the difference frequency is generated through a difference generation process as described with respect to FIG. 5.

A determination is made as to whether a response indicating the presence of an object under the ground is detected (operation 608). In operation 608, an object is not detected if a response is not detected. An object may still be present, but not detected because the third optical signal does not reflect off the object in a manner that results in a response that is detected.

If an object is detected as being present under the ground, an alert is generated (operation 610). The process terminates thereafter.

With reference again to operation 608, if an object is not detected as being present under the ground, a new location is identified (operation 612). The process then returns to operation 604 and operation 606 to transmit the first optical signal and the second optical signal at the new location.

The flowcharts and block diagrams in the different depicted embodiments illustrate the architecture, functionality, and operation of some possible implementations of apparatuses and methods in an illustrative embodiment. In this regard, each block in the flowcharts or block diagrams may represent a module, a segment, a function, and/or a portion of an operation or step. For example, one or more of the blocks may be implemented as program code, in hardware, or a combination of the program code and hardware. When implemented in hardware, the hardware may, for example, take the form of integrated circuits that are manufactured or configured to perform one or more operations in the flowcharts or block diagrams. In some alternative implementations of an illustrative embodiment, the function or functions noted in the blocks may occur out of the order noted in the figures. For example, in some cases, two blocks shown in succession may be executed substantially concurrently, or the blocks may sometimes be performed in the reverse order, depending upon the functionality involved. Also, other blocks may be added in addition to the illustrated blocks in a flowchart or block diagram.

For example, although not shown in the flowchart in FIG. 6, an operation also may be included to identify the object when a presence of the object is detected. As another illustrative example, if an object is not detected, a new value for the difference frequency may be selected and the first optical signal and the second optical signal may be transmitted to the same location. In this manner, difference frequencies may be selected to detect different types of objects in the same location.

Thus, one or more of the illustrative embodiments provide a method and apparatus for detecting objects that may be present under the surface of the ground. In these illustrative examples, difference frequency generation occurs as part of a nonlinear optical process when optical signals are transmitted into the ground. This difference frequency generation is used in the illustrative examples as described above to generate an optical signal that is able to penetrate the ground. Reflections are detected as a response to indicate the presence of an object under the ground.

Depending on the selection of the frequencies of the optical signals, the wavelengths of the optical signal with the difference frequency may penetrate tens of centimeters into the ground. In this manner, operators may detect objects under the ground. These objects may include tunnels, pipes, improvised explosive devices, and other objects.

The different illustrative examples may more efficiently detect objects as compared to currently used systems that use radio frequency signals. For example, the generation of the difference frequency does not rely on nonlinear properties of the object. Instead, one or more nonlinear properties of the ground are used to generate the optical signal with the difference frequency that penetrates the ground.

The description of the different illustrative embodiments has been presented for purposes of illustration and description, and is not intended to be exhaustive or limited to the embodiments in the form disclosed. Many modifications and variations will be apparent to those of ordinary skill in the art. Further, different illustrative embodiments may provide different features as compared to other illustrative embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

What is claimed is:

1. An apparatus comprising:
   a transmitter system configured to transmit a first optical signal having a first frequency and a second optical signal having a second frequency to a location on a surface of a ground such that the first optical signal and the second optical signal overlap each other at the location on the surface of the ground, wherein overlap of the first optical signal and the second optical signal at the location on the surface of the ground generates a third optical signal having a difference frequency that is a difference between the first frequency and the second frequency, and wherein the third optical signal is configured to travel into the ground; and
   a receiver system configured to detect a response to the third optical signal.

2. The apparatus of claim 1 further comprising:
   an information processor configured to determine whether an object is present in the ground using the response to the third optical signal.

3. The apparatus of claim 2, wherein the information processor is further configured to identify the object.

4. The apparatus of claim 1, wherein the third optical signal is a nonlinear response to the first optical signal and the second optical signal encountering components of the ground having a number of nonlinear optical properties.

5. The apparatus of claim 1, wherein the difference frequency is selected to penetrate the ground for a selected distance.

6. The apparatus of claim 1, wherein the transmitter system comprises:
   a coherent light source configured to generate first coherent light as the first optical signal and second coherent light as the second optical signal.

7. The apparatus of claim 6, wherein the transmitter system further comprises:
   an optical system configured to condition the first coherent light and the second coherent light for transmission to the location on the surface of the ground.

8. The apparatus of claim 7, wherein the optical system comprises:
   a polarizer configured to cause a first polarization in the first coherent light and a second polarization in the second coherent light.

9. The apparatus of claim 8, wherein the optical system further comprises:
   a frequency selector configured to pass the first coherent light with the first frequency and the second coherent light with the second frequency.

10. The apparatus of claim 1 further comprising:
    a controller configured to control the first frequency of the first optical signal and the second frequency of the second optical signal.

11. The apparatus of claim 1, wherein the receiver system comprises:
    a light detection system.

12. The apparatus of claim 1 further comprising:
    a platform, wherein the transmitter system and the receiver system are associated with the platform.

13. The apparatus of claim 2, wherein the object is selected from one of an improvised explosive device, contraband, a box, a tunnel, a pipe, a wire, a cable, and a container.

14. A method for detecting an object, the method comprising:
- transmitting a first optical signal having a first frequency to a location on a surface of a ground;
- transmitting a second optical signal having a second frequency to the location on the surface of a ground such that the first optical signal and the second optical signal overlap each other at the location on the surface of the ground, wherein overlap of the first optical signal and the second optical signal at the location on the surface of the ground generates a third optical signal having a difference frequency that is a difference between the first frequency and the second frequency, and wherein the third optical signal is configured to travel into the ground;
- detecting a response to the third optical signal; and
- determining whether an object is present in the ground using the response to the third optical signal.

15. The method of claim 14 further comprising:
generating an alert when the object is present in the ground.

16. The method of claim 15 further comprising:
identifying the object when the object is present in the ground.

17. The method of claim 14 further comprising:
- identifying a value for the difference frequency; and
- selecting the first frequency and the second frequency based on the difference frequency.

18. The method of claim 17, wherein the value for the difference frequency is identified based on at least one of a number of properties of the ground and a number of properties of the object.

19. The method of claim 14, wherein the first optical signal is a first collimated beam of first coherent light and the second optical signal is a second collimated beam of second coherent light.

20. The method of claim 14, wherein the first optical signal and the second optical signal are transmitted by a transmitter system and the response is detected by a receiver system.

* * * * *